(12) United States Patent
Del Giglio

(10) Patent No.: US 8,298,162 B2
(45) Date of Patent: Oct. 30, 2012

(54) SKIN AND ADIPOSE TISSUE TREATMENT BY NONFOCALIZED OPPOSING SIDE SHOCK WAVES

(76) Inventor: Antonio Del Giglio, Verona (IT)

( * ) Notice: Subject to any disclaimer, the term of this patent is extended or adjusted under 35 U.S.C. 154(b) by 1198 days.

(21) Appl. No.: 11/594,424

(22) Filed: Nov. 8, 2006

(65) Prior Publication Data

US 2008/0009885 A1    Jan. 10, 2008

(51) Int. Cl.
*A61H 1/00*    (2006.01)

(52) U.S. Cl. ....... 601/2; 601/3; 601/4; 606/2.5; 606/128

(58) Field of Classification Search .................. 601/2, 3, 601/4; 606/128, 2.5

See application file for complete search history.

(56) References Cited

U.S. PATENT DOCUMENTS

| | | |
|---|---|---|
| 3,942,531 A | 3/1976 | Hoff et al. |
| 4,957,099 A | 9/1990 | Hassler |
| 4,958,639 A | 9/1990 | Uchiyama et al. |
| 5,005,579 A | 4/1991 | Wurster |
| 5,143,063 A | 9/1992 | Fellner |
| 5,178,135 A | 1/1993 | Uchiyama et al. |
| 5,209,221 A | 5/1993 | Riedlinger |
| 5,219,401 A | 6/1993 | Cathignol et al. |
| 5,358,466 A | 10/1994 | Aida et al. |
| 5,374,236 A | 12/1994 | Hassler |
| 5,381,792 A | 1/1995 | Yanagida et al. |
| 5,431,621 A | 7/1995 | Dory |
| 5,501,655 A | 3/1996 | Rolt et al. |
| 5,582,578 A | 12/1996 | Zhong et al. |
| 5,725,482 A | 3/1998 | Bishop |
| 6,071,239 A | 6/2000 | Cribbs et al. |
| 6,123,679 A | 9/2000 | Lafaut et al. |
| 6,254,553 B1 | 7/2001 | Lidgren et al. |
| 6,450,972 B1 | 9/2002 | Knoll |
| 6,500,141 B1 | 12/2002 | Irion et al. |
| 6,595,934 B1 | 7/2003 | Hissong et al. |
| 6,607,498 B2 | 8/2003 | Eshel |
| 7,559,904 B2 * | 7/2009 | Ein-Gal ........................ 601/2 |
| 2003/0215046 A1 * | 11/2003 | Hornkohl ................... 376/100 |
| 2005/0054955 A1 * | 3/2005 | Lidgren ........................ 601/2 |

FOREIGN PATENT DOCUMENTS

| | | |
|---|---|---|
| EP | 0756879 | 2/1997 |
| WO | WO93/24066 | 12/1993 |
| WO | WO96/40369 | 12/1996 |

* cited by examiner

*Primary Examiner* — Brian Casler
*Assistant Examiner* — Daniel Huntley
(74) *Attorney, Agent, or Firm* — Michael I. Kroll

(57) ABSTRACT

The present invention is a device for the destruction of adipose tissue comprising two or more ultrasound generators positioned on opposing sides of the treatment area each generating a non-focused wave that converge forming a interferential clash zone with the treatment area therein. Ultrasound generators are contained within a handpiece housing. Furthermore the present invention provides an optional housing having a source of vacuum for encompassing a treatment area whereby the treatment area is drawn bell-shaped into the housing whereupon a pair of shock wave generators are energized to produce cavitational areas within the treatment area and a third interferential energized area between the cavitational areas.

8 Claims, 8 Drawing Sheets

SKIN AND ADIPOSE TISSUE TREATMENT BY NONFOCALIZED OPPOSING SIDE SHOCK WAVES

BACKGROUND OF THE INVENTION

RELATED APPLICATIONS

This application is subject to Italian patent application no. VR 2006A000113 filed 06 Jul. 2006—inventor Antonio Del Giglio and claims the priority benefit under 35 U.S.C. sctn. 119 (a).

1. Field of the Invention

The present invention relates generally to medical devices and, more specifically, to a device for the destruction of adipose tissue comprising two or more ultrasound generators positioned on opposing sides of the treatment area each generating a non-focused wave that converge forming an interferential clash zone with the treatment area therein. The ultrasound generators are contained within a handpiece housing.

Furthermore, the present invention provides an optional housing having a source of vacuum for encompassing a treatment area whereby the treatment area is drawn bell-shaped into the housing whereupon a pair of shock wave generators are energized to produce cavitational areas within the treatment area and a third interferential energized area between the cavitational areas.

Various types of devices have been used for treatment of adipose tissue. Most of these methods rely upon the fact that adipose tissue is less durable mechanically than other body tissues such as skin and muscles. The problem is that adipose tissue is located under the skin layer and energy applied to degrade adipose tissue must reach the adipose tissue without damaging the skin.

One method to reduce fat is liposuction or liposculture which is based on suction of fat out of the body. As adipose cells do not regenerate; the reduction is stable. The disadvantage of this method is its invasive character and possible complications of surgery.

U.S. Pat. No. 4,958,639 discloses destruction of calculi in the kidney using shock waves.

U.S. Pat. No. 5,143,063 describes a method of treating adipose tissue based on thermal destruction of fat by exposing adipose tissue to focused microwave or ultrasound waves. The intensity of the energy is determined so as to selectively destroy fat cells without damaging the skin or deep tissues.

U.S. Pat. No. 5,725,482 discloses superposition of ultrasound waves from two or more sources to create a wave having high intensity localized at the adipose tissue to be treated.

U.S. Pat. No. 6,450,972 discloses a device for ultrasound irradiation of adipose tissue in which the ultrasound waves are not focused, but the intensity of the waves is chosen for selective lipolysis.

U.S. Pat. No. 6,500,141 improves treatment safety with ultrasound by forming the skin surface using suction.

2. Description of the Prior Art

There are other acoustical device designed for adipose treatment. Typical of these is U.S. Pat. No. 3,942,531 issued to Hoff, et al. on Mar. 9, 1976.

Another patent was issued to Hassler on Sep. 18, 1990 as U.S. Pat. No. 4,957,099. Yet another U.S. Pat. No. 4,958,639 was issued to Uchiyama, et al. on Sep. 25, 1990 and still yet another was issued on Apr. 9, 1991 to Wurster, et al. as U.S. Pat. No. 5,005,579.

Another patent was issued to Fellner on Sep. 1, 1992 as U.S. Pat. No. 5,143,063. Yet another U.S. Pat. No. 5,178,135 was issued to Uchiyama, et al. on Jan. 12, 1993. Another was issued to Riedlinger on May 11, 1993 as U.S. Pat. No. 5,209,221 and still yet another was issued on Jun. 15, 1993 to Cathignol, et al. as U.S. Pat. No. 5,219,401.

Another patent was issued to Aida, et al. on Oct. 25, 1994 as U.S. Pat. No. 5,358,466. Yet another U.S. Pat. No. 5,374,236 was issued to Hassler on Dec. 20, 1994. Another was issued to Yanagida, et al. on Jan. 17, 1995 as U.S. Pat. No. 5,381,792 and still yet another was issued on Jul. 11, 1995 to Dory as U.S. Pat. No. 5,431,621.

Another patent was issued to Rolt, et al. on Mar. 26, 1996 as U.S. Pat. No. 5,501,655. Yet another U.S. Pat. No. 5,582,578 was issued to Zhong, et al. on Dec. 10, 1996. Another was issued to Bishop on Mar. 10, 1998 as U.S. Pat. No. 5,725,482 and still yet another was issued on Jun. 6, 2000 to Cribbs, et al. as U.S. Pat. No. 6,071,239.

Another patent was issued to Lafaut, et al. on Sep. 26, 2000 as U.S. Pat. No. 6,123,679. Yet another U.S. Pat. No. 6,254,553 was issued to Lidgren, et al. on Jul. 3, 2001. Another was issued to Knoll on Sep. 17, 2002 as U.S. Pat. No. 6,450,972 and still yet another was issued on Dec. 31, 2002 to Irion, et al. as U.S. Pat. No. 6,500,141.

Another patent was issued to Hissong, et al. on Jul. 22, 2003 as U.S. Pat. No. 6,595,934. Yet another U.S. Pat. No. 6,607,498 was issued to Eshel on Aug. 19, 2003. Another was published to Rosso on Dec. 9, 1993 as International Patent Application No. WO 93/24066. Another was published on Dec. 19, 1996 to Richards as International Patent Application No. WO 96/40369 and still yet another was published on Feb. 5, 1997 to Cafiero Franconi as European Patent Application No. EP0756879.

U.S. Pat. No. 3,942,531

Inventor: Gunter Hoff, et al.

Issued: Mar. 9, 1976

This invention relates to an apparatus for breaking-up, without contact, concrements present in the body of a living being, which comprises waveguide means filled with a liquid medium and adapted to be placed against said body, and means for generating shock waves within said waveguide means.

U.S. Pat. No. 4,957,099

Inventor: Dietrich Hassler

Issued: Sep. 18, 1990

A shock wave source for an extracorporeal lithotripsy system has a number of electro-acoustic transducers arranged in a concave surface, each transducer having an acoustic axis, and the shock wave source having an acoustic axis. The transducers are each pivotally mounted, and a common adjusting element is provided which pivots each of the transducers so that their acoustic axes intersect at a focus, which lies on the acoustic axis of the shock wave source. The common element also permits adjustment of the location of the focus along the shock wave source acoustic axis so as to be more distal or more proximate relative to the shock wave source.

U.S. Pat. No. 4,958,639

Inventor: Naoki Uchiyama

Issued: Sep. 25, 1990

An ultrasonic therapeutical apparatus observes the interior of a living body utilizing an ultrasonic wave, allows a location signal to be generated on the basis of an output from the observation system, and controls a focus shifting system in accordance with the location signal. Subsequently, a shock wave generating system is driven to generate an ultrasonic shock wave, which is directed to a focal point, thereby crushing a calculus.

U.S. Pat. No. 5,005,579

Inventor: Helmut Wurster

Issued: Apr. 9, 1991

Apparatus for spatial location and destruction of an object inside a patient's body by means of ultrasound transmitted to the patient's body via a coupling fluid, the apparatus comprises a focusing transducer for generating the ultrasound piezoelectrically to destroy the object, at least two transmitting and receiving locating transducers for locating the object under visual observation, said at least two locating transducers being incorporated, installed or mounted in said focusing transducer and being operable to generate B-images which are displayed optionally individually and/or in combination as a spatial image on at least one monitor, there being preferably, three such locating transducers for generating the B-images.

U.S. Pat. No. 5,143,063

Inventor: Donald G. Fellner

Issued: Sep. 1, 1992

Electromedical apparatus is employed to non-invasively remove adipose tissue from the body by causing necrosis thereof by localizing (e.g., focusing) radiant energy. The radiant energy may be of any suitable kind, for example, localized radio frequency, microwave or ultrasound energy, which is impinged upon the cells to be eliminated. Cell destruction occurs through a mechanism such as, e.g., heating or mechanical disruption beyond a level which the adipose tissue can survive.

U.S. Pat. No. 5,178,135

Inventor: Naoki Uchiyama, et al.

Issued: Jan. 12, 1993

A therapeutical apparatus includes a measuring apparatus including a probe which generates an X-ray or ultrasonic wave in order to detect the location of a target to be treated such as calculi situated within the kidney, liver, biliary ducts. A therapeutical energy generator generates a shock wave of sufficient energy for purpose of therapy externally of the physical body and focuses it upon the target. Structure is provided for causing a displacement of the generator and the measuring apparatus around the surface of a patient. Structure is provided to activate the generator.

U.S. Pat. No. 5,209,221

Inventor: Rainer Riedlinger

Issued: May 11, 1993

A device for generating sonic signal forms for limiting, preventing or regressing the growth of pathological tissue comprises an ultrasonic transmission system for transmitting sound waves, focussed on the tissue to be treated, by way of a coupling medium. An ultrasonic signal produced at the focus of the system comprises brief pulses having at least one rarefaction phase with a negative sonic pressure amplitude with a value greater than 2.times. 10.sup.5 Pa. The ultrasonic signal is radiated with a carrier frequency exceeding 20 kHz, a sonic pulse duration T of less than 100 .mu.s and a pulse recurrence rate of less than 1/(5T). The device produces controlled cavitation in the tissue to be treated.

U.S. Pat. No. 5,219,401

Inventor: Dominique Cathignol

Issued: Jun. 15, 1993

The invention relates to an apparatus for selective destruction of cells including soft tissues and bones inside a living subject's body. This apparatus is characterized in that it comprises: means for generating gas bubbles in situ within the cells to be selectively destroyed, and implosion means capable of provoking the implosion in situ of the gas bubbles, thereby destroying the cells to be destroyed which are adjacent the imploded gas bubbles. The invention makes it possible to destroy cells inside a living subject's body by a non-invasive and extracorporeal and also extremely simple and efficient way, further permitting the treatment of metastases.

U.S. Pat. No. 5,358,466

Inventor: Satoshi Aida, et al.

Issued: Oct. 25, 1994

An apparatus for destroying a calculus includes an ultrasonic wave generating unit capable of setting a plurality of piezo-electric devices in a drive/reception mode by phase control, a peak value detecting unit for detecting a peak value, in a predetermined time width, of an echo signal in a reception signal received by the piezo-electric devices, a first comparing unit for comparing the peak value detected by the peak value detecting unit with a first predetermined threshold value, a frequency analyzing unit for analyzing a frequency component, in the predetermined time width, of the echo signal in the reception signal, a calculating unit for calculating a predetermined characteristic value on the basis of frequency component data obtained by the frequency analyzing unit, a second comparing unit for comparing the characteristic value obtained by the calculating unit with a second predetermined threshold value, and a display unit for displaying a comparison result of the first comparing unit with a comparison result of the second comparing unit.

U.S. Pat. No. 5,374,236

Inventor: Dietrich Hassler

Issued: Dec. 20, 1994

An electromagnetic pressure pulse source for generating focused pressure pulses as an electrically conductive membrane and a coil system which drives the membrane by rapidly displacing the membrane from the coil system. The coil system is formed by an annular array having a number of annular zones which can be individually activated to cause the generation of pressure pulses in variable chronological relation to each other, which permits the location of the focus of the resulting shockwave to be adjusted with a range, and/or the diameter of the focus to be changed.

U.S. Pat. No. 5,381,792

Inventor: Jan. 17, 1995

Issued: Jan. 17, 1995

In a shock wave generating apparatus, phase shifts contained in echo signals reflected from a calculus are corrected in order to clearly judge whether or not such a calculus is actually present at a focal point or a near region. The shock wave generating apparatus includes: a shock wave producing unit constructed of at least two transducer elements, for producing shock wave pulses used to disintegrate an object located near a focal point of said shock wave producing unit within a biological body under medical examination upon receipt of first drive pulses having first energy levels, and also for producing ultrasonic pulses used to obtain echo pulses reflected from said object near the focal point, as echo signals, upon receipt of second drive pulses having second energy levels lower than said first energy levels of the first drive pulses; an analog type phase-shift correcting unit for correcting phase shifts contained in the echo signals reflected from the object near the focal point by making respective phases of the echo signals coincident with each other as to a time domain of the analog echo signals, thereby obtaining an analog phase-corrected echo signal; a peak detecting unit for detecting a peak value of the analog phase-corrected echo signal; and a controlling unit for controlling the shock wave producing unit based on the peak value of the analog phase-corrected echo signal to determine whether or not the shock wave pulses are produced in order to destroy the object near the focal point.

U.S. Pat. No. 5,431,621

Inventor: Jacques Dory

Issued: Jul. 11, 1995

A Process and device of location and destruction of an anatomic target includes the periodic emission of a focused treatment beam of elastic waves and an echographic image of the target formed in real time during the treatment period by means of an ultrasonic auxiliary beam carrying out a scanning substantially centered in a symmetry plane of the focused treatment beam. Also displayed superimposed on the target image is a mark showing the theoretical position of the focal point of the treatment beam. Selection of the image forming echoes reflected from the target as a function of the coordinates of the region of impact of the auxiliary beam with respect to the echographic source is effected and the treatment and auxiliary sources are simultaneously displaced under the control of signals derived from the selected echoes until the coincidence between the image of the mark and the image of the target object is reached where the treatment beam emission is then triggered.

U.S. Pat. No. 5,501,655

Inventor: Kenneth D. Rolt, et al.

Issued: Mar. 26, 1996

An ultrasound hyperthermia applicator suitable for medical hyperthermia treatment, and method for using the same, includes two ultrasound sources producing focused ultrasound beams of frequencies $f_0$ and $f_1$. An aiming device directs the two ultrasound beams so that they cross each other confocally at the target. A controller activates the two ultrasound sources so that the target is simultaneously irradiated by the two focused ultrasound beams. The two ultrasound sources provide acoustic energy sufficient to cause significant intermodulation products to be produced at the target due to the interaction of the two ultrasound beams. The intermodulation products are absorbed by the target to enhance heating of the target. In preferred embodiments the ultrasound sources include pair of signal generator for producing gated ultrasound output signals driving single crystal ultrasound transducers. In other embodiments the ultrasound sources include a pair of phased array ultrasound transducers for generating two steerable ultrasound beams. An aiming device is provided for electronically steering and focusing the two ultrasound beams so that they cross each other confocally at the target. Further embodiments employ pluralities of transducers, arrays, or both.

U.S. Pat. No. 5,582,578

Inventor: Pei Zhong, et al.

Issued: Dec. 10, 1996

The invention relates to a method for the comminution of concretions in vivo by controlled, concentrated cavitation energy. This method utilizes two shock wave pulses with a specified time delay and pressure relationship, with the first shock wave pulse being used to induce a transient cavitation bubble cluster near the target concretion, and the second shock wave pulse to control and force the collapse of the cavitation bubble cluster towards the target concretion with concentrated energy deposition, while avoiding injury to surrounding tissue caused by random collapse of the cavitation bubbles. This invention makes it possible to significantly enhance the fragmentation efficiency of the concretion using shock waves while reducing potential deleterious injury to surrounding tissue.

U.S. Pat. No. 5,725,482

Inventor: Richard P. Bishop

Issued: Mar. 10, 1998

A method for focussing vibrational energy upon a target volume within a surrounding contiguous medium imparts high intensity energy upon the target volume from low level energy sources. A plurality of standing compression waves are established within the medium along corresponding longitudinal axes between opposing pairs of coordinated transducers. The target volume is located at the common intersection of the axes of the standing compression waves. Opposing pairs of transducers are positioned from each other at a distance equal to an integer multiple of half wavelengths of the corresponding standing wave therebetween. The phase angle of each standing compression wave is regulated so as to cause each wave to be at its maximum intensity (amplitude) within the target volume at the point of common intersection with the other standing waves. The plurality of intersecting standing waves constructively interfere within the target volume, thereby imparting more intense vibrational energy upon the target volume that upon the surrounding medium.

U.S. Pat. No. 6,071,239

Inventor: Robert W. Cribbs, et al.

Issued: Jun. 6, 2000

Fat cells in a living patient are noninvasively destroyed without separating the skin from the body by applying to the fat layer high intensity focused ultrasound simultaneously in a multiplicity of discrete focal zones produced by a single transducer array. A novel phasing apparatus for producing a widely variable set of focal zone patterns for lipolytic therapy and other purposes is disclosed.

U.S. Pat. No. 6,123,679

Inventor: Jean-Pierre Lafaunt, et al.

Issued: Sep. 26, 2000

A method for extracorporeal shock wave lithotripsy comprises the steps of applying to a concretion to be disintegrated an acoustic shock wave and applying to the concretion to be disintegrated in sequence to said acoustic shock wave an oscillating acoustic pressure wave train having a pressure amplitude, said oscillating acoustic wave train having at least one amplitude maximum and at least one amplitude minimum.

U.S. Pat. No. 6,254,553

Inventor: Lars Lidgren, et al.

Issued: Jul. 3, 2001

The present invention relates to a device for non-invasive treatment of biological tissue, whereby the treatment aim at changing or degenerating said tissue. This device has a treatment transducer (2) comprising at least one ultrasonic transducer (3 and/or 4) which is provided to treat intervertebral discs (1), preferably nucleus pulposus (1$a$), by means of ultrasound, whereby the ultrasonic field of the ultrasonic transducer (3 and/or 4) is focused in said intervertebral disc (1), preferably in nucleus pulposus (1$a$), for heating the tissue therein, to such temperatures that the tissue in the focal area (5) degenerates, whereby the pressure in the intervertebral disc (1) and thus, the pressure against the spinal cord (6) is reduced.

U.S. Pat. No. 6,450,972

Inventor: Meinhard Knoll

Issued: Sep. 17, 2002

The invention relates to a sensor system for measuring pressure profiles. Such systems can be used wherever pressure distributions in one or two dimensions are to be measured. An important field of application is medicine. Here pressure profile measurements, e.g. in urology, proctology, cardiology and other disciplines can be carried out with the aid of catheters. The measuring catheter is formed as a tubular flexible hollow body (1) of length L. An outer pressure load p(x) is represented on tube (1) as a cross-sectional function A(x). The local cross-section A(x) is scanned by the tube being filled from one side at (x=0) continuously with a liquid substance (I) which displaces substance (II) to the filling length X.sub.A. The filling length x.sub.A can be measured according to differing methods: measurement of the electrical resistance, measurement of the electrical capacity, measurement of acoustic resonance.

U.S. Pat. No. 6,500,141

Inventor: Klaus M. Irion, et al.

Issued: Dec. 31, 2002

An apparatus for treating body tissue, in particular superficial soft tissue, with ultrasound, comprises an ultrasonic generation unit and an applicator, by means of which the ultrasound can be irradiated from an applicator surface facing the body surface from outside through the body surface into the body tissue. A suction apparatus for sucking in the body surface against the applicator surface is provided.

U.S. Pat. No. 6,595,934

Inventor: James B. Hissong, et al.

Issued: Jul. 22, 2003

A method of skin rejuvenation by thermal ablation using high intensity focused ultrasound energy includes the steps of positioning an ultrasound emitting member adjacent an external surface of the skin, emitting ultrasound energy from the ultrasound emitting member into the skin, focusing the ultrasound energy in the skin, ablating the skin with the focused ultrasound energy to form an ablated tissue area below the external surface of the skin containing unablated tissue of the skin and a plurality of lesions at which the tissue of the skin is ablated, and removing the ultrasound emitting member from adjacent the external surface of the skin. The lesions cause collagen production by the skin to be stimulated. The lesions can begin and end at predetermined depths beneath the external surface of the skin so that the epidermis and the deep layer of the dermis are not damaged.

U.S. Pat. No. 6,607,498

Inventor: Yoram Eshel

Issued: Aug. 19, 2003

A method and apparatus for producing lysis of adipose tissue underlying the skin of a subject, by: applying an ultrasonic transducer to the subject's skin to transmit therethrough ultrasonic waves focused on the adipose tissue; and electrically actuating the ultrasonic transducer to transmit ultrasonic waves to produce cavitational lysis of the adipose tissue without damaging non-adipose tissue.

International Patent Application Number WO 93/24066

Inventor: Luciano Rosso, et al.

Published: Dec. 9, 1993

Method and apparatus for the cosmetical treatment of the human body through removal of the adipose tissue masses by means of the combined effect of the infiltration of a diluent solution and the application of a fluidizing perturbation within the adipose tissue (A), so as to enable the subsequent extraction thereof. The fluidizing perturbation is generated by the emission of electromagnetic waves by means of a pair of electrodes, at least one of which is directly associated to a tubular perforator (9, 10) through which the diluent solution is infiltrated and/or the fluidized adipose tissue is extracted.

International Patent Application Number WO96/40369

Inventor: William F. Richards, et al.

Published: Dec. 19, 1996

An apparatus and method for non-invasive removal of target tissues, is disclosed. The apparatus includes a microwave applicator antenna element array (20) for introducing a plurality of cylindrical, quasi-transverse electromagnetic surface waves adjacent the target tissue. Through successive phase shifts, the electromagnetic surface waves are brought to converge on a focal point within the target tissue, thereby elevating the temperature of the tissue. In one application the microwave applicator is used for reducing fatty tissue within a subcutaneous fatty layer by taking into account the differing dielectric constants of the adjacent skin and muscle layers. By launching a wave trapped between the skin layer and the muscle layers, a converging cylindrical wave is produced which includes a column of high density along a line extending from the skin fat interface to the muscle fat interface. The effect of the column of high density is to raise the temperature of adipose cells to a level at which fat cell necrosis occurs. In operation, a cooling bolus (34) coupled to the applicator actively maintains skin surface temperature below a level at which cell damage or discomfort would occur.

European Patent Application Number EP 0 756 879

Inventor: Cafiero Franconi

Published: Feb. 5, 1997

The shields concern all short-wave or microwave electromagnetic applicators for thermotherapy in oncology, physical medicine, cosmetology, urology, veterinary medicine and pharmacokinetics, to produce improved heating efficiency and penetration, improved treatment comfort and lower electromagnetic risk to patient's critical organs and to operators. Shields envelopes applicators and parts of body regions producing EM enclosures of containment of radiation leakages. External hood shields block lateral and backward leakages. Regional shields block also leakages through the exposed tissues. Inner shields trap spurious applicators electric fields keeping them away from overheating the patient's adipose. The passive shields protect adjacent critical organs from the treatment fields. The regional shield (26) envelopes both applicator (3) and body region (2) encompassing target (1) heated with beam (10) through the air-gap (8) and establishing the EM enclosure (27) of containment of the EM energy diffused by (3), which blocks the dispersion of the lateral beam fraction (12) through (8) and of the beam fraction (11) that crosses target (1).

While these treatment systems may be suitable for the purposes for which they were designed, they would not be as suitable for the purposes of the present invention, as hereinafter described.

SUMMARY OF THE PRESENT INVENTION

The present invention provides a method and apparatus for the treatment of adipose tissue. In accordance with the invention, sonic non-focused shock waves are directed at a region of subcutaneous fat to be destroyed. The energy of the non-focused shock waves is selected on the thickness of the adipose tissue layer.

The non-focused shock waves are generated with the described device and will destroy the fat tissue on the cavitational volumetric area ellipsoid shaped at the clash point of the shock waves that are generated at opposite locations.

The present invention does not need any focusing system as the cavitational area generated by the shockwave occurs within the desired subcutaneous area and the clash point of the shock waves also occurs within the targeted adipose tissue.

A primary object of the present invention is to provide a device for the non-invasive destruction of subcutaneous adipose tissue.

Another object of the present invention is to provide a device for adipose tissue treatment having a pulse generation serving as a control unit for the adipose tissue treatment having a control panel for selectively varying treatment parameters.

Yet another object of the present invention is to provide a device for adipose tissue treatment having at least one hand held applicator.

Still yet another object of the present invention is to provide a device for adipose tissue treatment wherein said hand held applicator comprises a housing incorporating a shock wave generator in electrical communication with the pulse generator.

Another object of the present invention is to provide a device for adipose tissue treatment wherein said hand held applicator has a membrane whereby said applicator can be applied directly to the skin of a desired treatment area.

Yet another object of the present invention is to provide a device for adipose tissue treatment having an applicator comprising a housing having opposing shock wave generators and a port for attachment of a vacuum source whereby a desired treatment area can be drawn into the housing between the opposing shock wave generators.

Still yet another object of the present invention is to provide a device for adipose tissue treatment wherein opposing shock wave applicators use non-focused sonic waves to create an applicator cavitational zone and a third interferential energy clash zone between the applicators cavitational zones.

Additional objects of the present invention will appear as the description proceeds.

The present invention overcomes the shortcomings of the prior art by providing a device for the destruction of adipose tissue comprising two or more ultrasound generators positioned on opposing sides of the treatment area each generating a non-focused wave that converge forming an interferential clash zone with the treatment area therein. Ultrasound generators are contained within a handpiece housing. Furthermore, the present invention provides an optional housing having a source of vacuum for encompassing a treatment area whereby the treatment area is drawn bell-shaped into the housing whereupon a pair of shock wave generators are energized to produce cavitational areas within the treatment area and a third interferential energized area between the cavitational areas.

The foregoing and other objects and advantages will appear from the description to follow. In the description reference is made to the accompanying drawings, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWING FIGURES

In order that the invention may be more fully understood, it will now be described, by way of example, with reference to the accompanying drawing in which.

DETAILED DESCRIPTION OF THE PREFERRED EMBODIMENT

The following discussion describes in detail one embodiment of the invention ( and several variations of that embodiment). This discussion should not be construed, however, as limiting the invention to those particular embodiments, practitioners skilled in the art will recognize numerous other embodiments as well. For definition of the complete scope of the invention, the reader is directed to appended claims.

Figure 1:
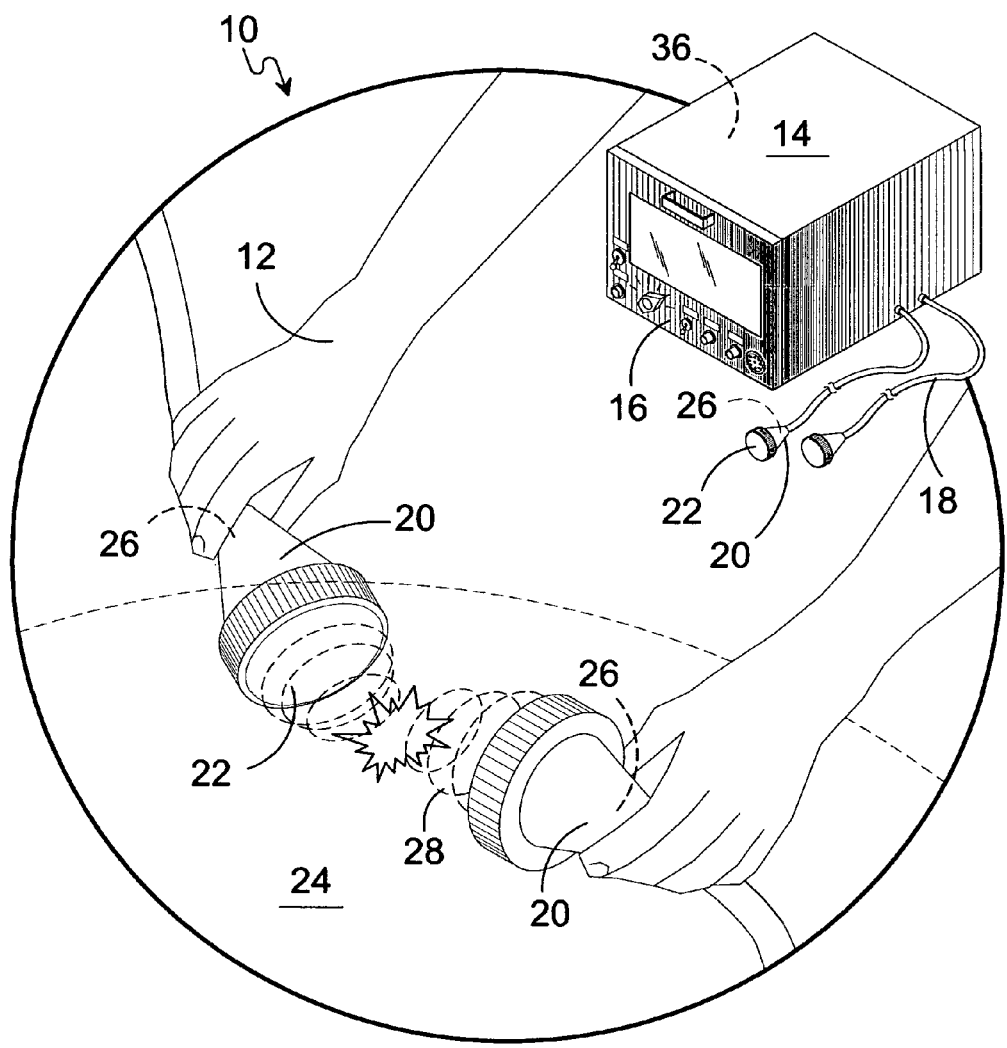
FIG. 1 is an illustrative view of the present invention in use.

Referring to FIG. 1, shown is an illustrative view of the present invention in use. Shown is a device 10 for applying essentially non-focused shock waves 28 to adipose tissue 24, in accordance with the invention. A handheld applicator 20 contains one or more sources 26 of acoustic waves and is designed to be applied directly to the skin 24 of a treatment area containing unwanted adipose tissue. The applicator 20 is connected 18 to a pulse generator 14 serving as control unit having a control panel 16 whereby an operator 12 can selectively set parametric values for the treatment including shock wave intensity, rate frequency, pulse duration and wave Hz selection and wherein said values are display on the control panel LCD display. The pulse generator 14 sends the electrical pulse to the applicator 20 via electrical leads 18. Optionally, the pulse generator 14 can incorporate a processor 36 for monitoring and controlling various functions of the device.

Figure 2:
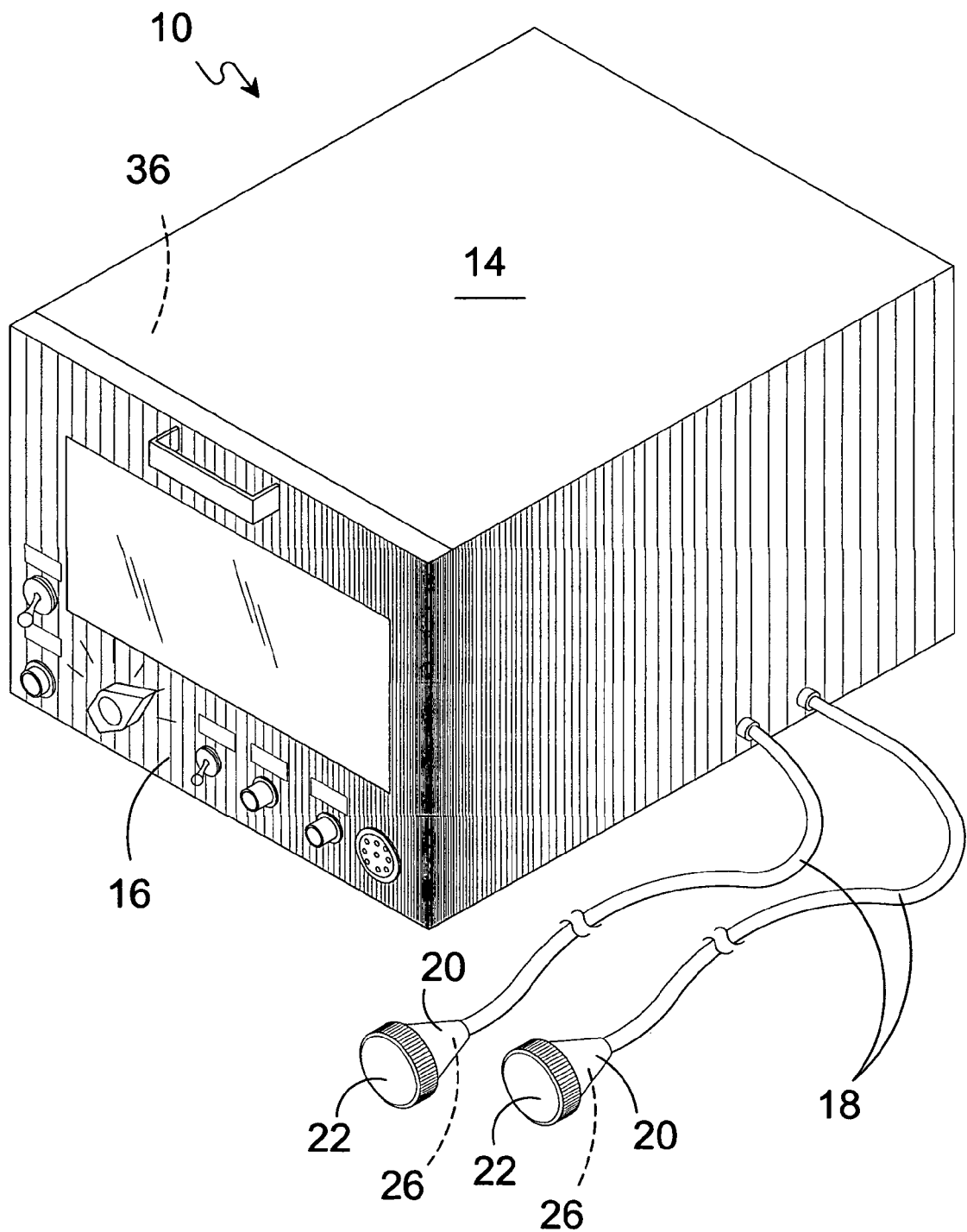
FIG. 2 is a perspective view of the pulse generator of the present invention.

Referring to FIG. 2, shown is a perspective view of the pulse generator of the present invention. The pulse generator 14 serves as control unit for varying adipose tissue treatment 10 parameters via control panel 16 including shock wave intensity, rate frequency, pulse duration and wave Hz selection and wherein said values are display on the control panel LCD display. The pulse generator 14 is in electrical communication 18 with at least one handheld applicator 20 that is applied 22 directly to the skin 24 and contains one or more sources of acoustic waves 26 for generating non-focused shock waves used to destroy adipose tissue within the applicator treatment area. Additionally, the pulse generator can incorporate a processor 36 for monitoring and controlling various functions of the device.

Figure 3:
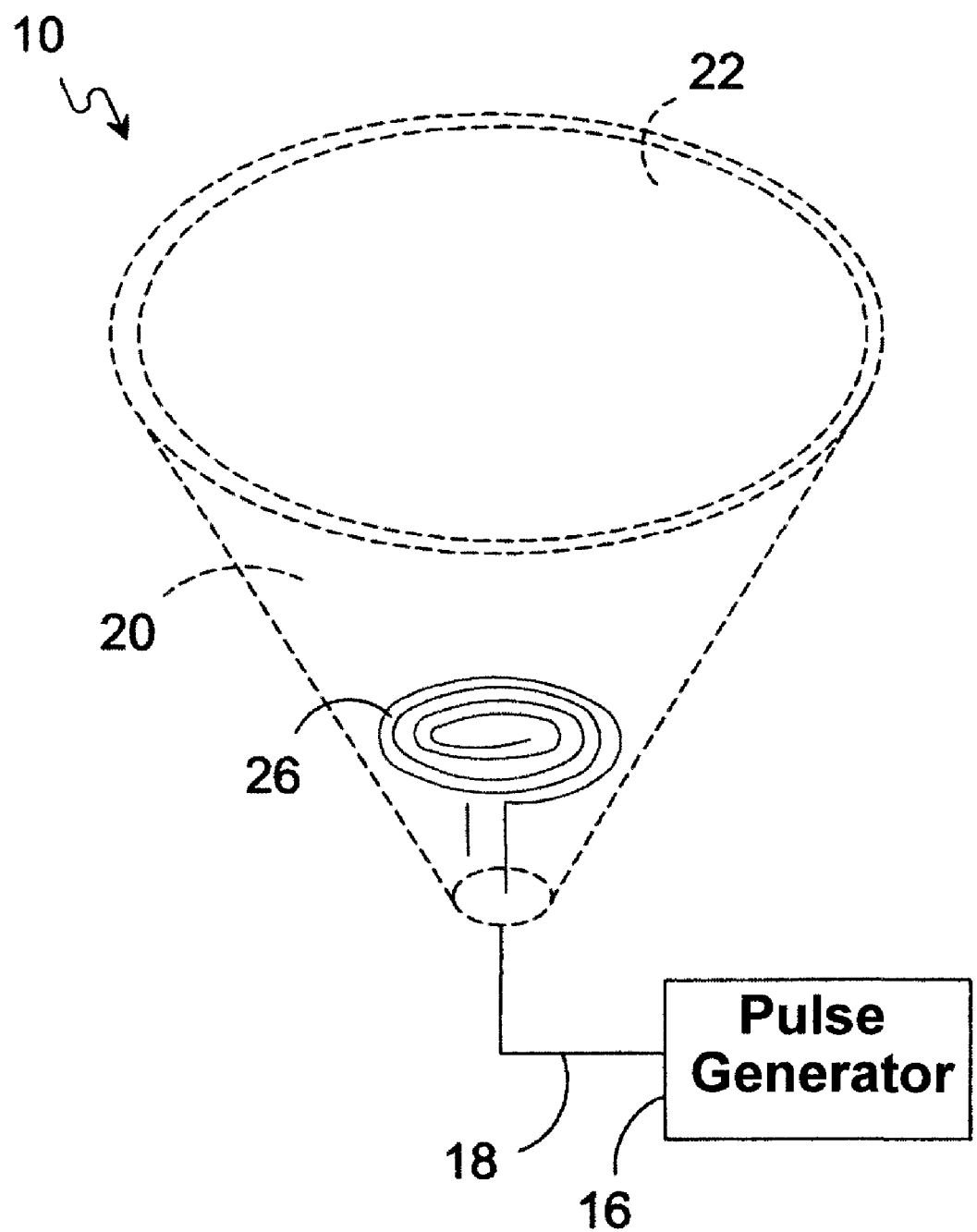
FIG. 3 is a perspective view of an applicator on the present invention.

Referring to FIG. 3, shown is a perspective view of an applicator on the present invention 10. The applicator 20 has a housing containing the coil 26 of the shock wave generator which is in electrical communication 18 with the pulse generator 14. When a voltage pulse is applied to the applicator coil 26 an electrical discharge generates a non-focused sonic shock wave 28 that emanates from the applicator 20. The applicator housing 20 has a membrane 22 with acoustic properties similar to body tissue that provides an interface between the applicator and the region to be treated. A medium such as oil, water or a water-based gel may be used for acoustic coupling between the applicator membrane 22 and the skin 24.

Figure 4:
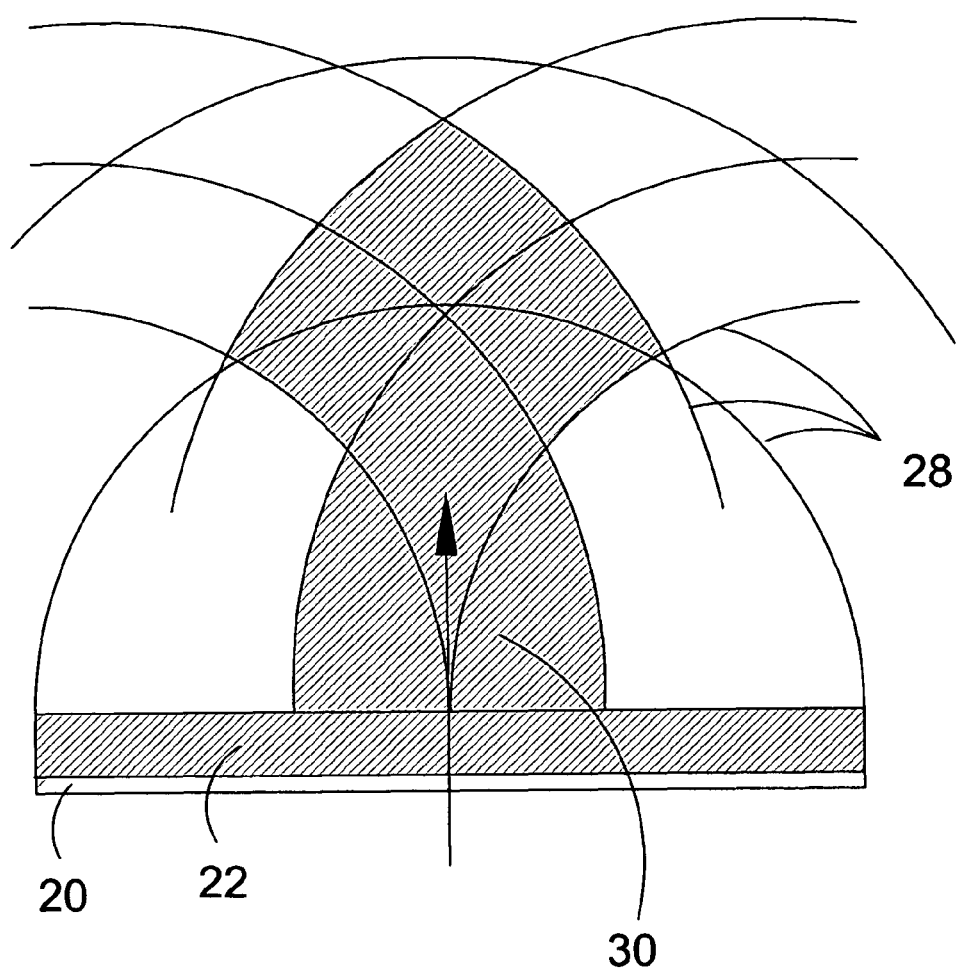
FIG. 4 is an illustrative view of the shock waves emanating from the applicator.

Referring to FIG. 4, shown is an illustrative view of the shock waves emanating from the applicator. The typical structure of a shock is composed of a high pressure wave that passes through the tissue according to the physical laws governing the kinetics of sound in liquid and the second is the contemporary creation of a high negative pressure attached to the tail of the positive pressure wave. The resulting wave 28 is the addition of the two pressure differentials creating the shock wave cavitational area 30. The effect created by the non-focused shock wave 28 is the critical cavitational zone that starts out from the resonance membrane 22 of the handheld applicator 20 shaped as a conus.

Figure 5:
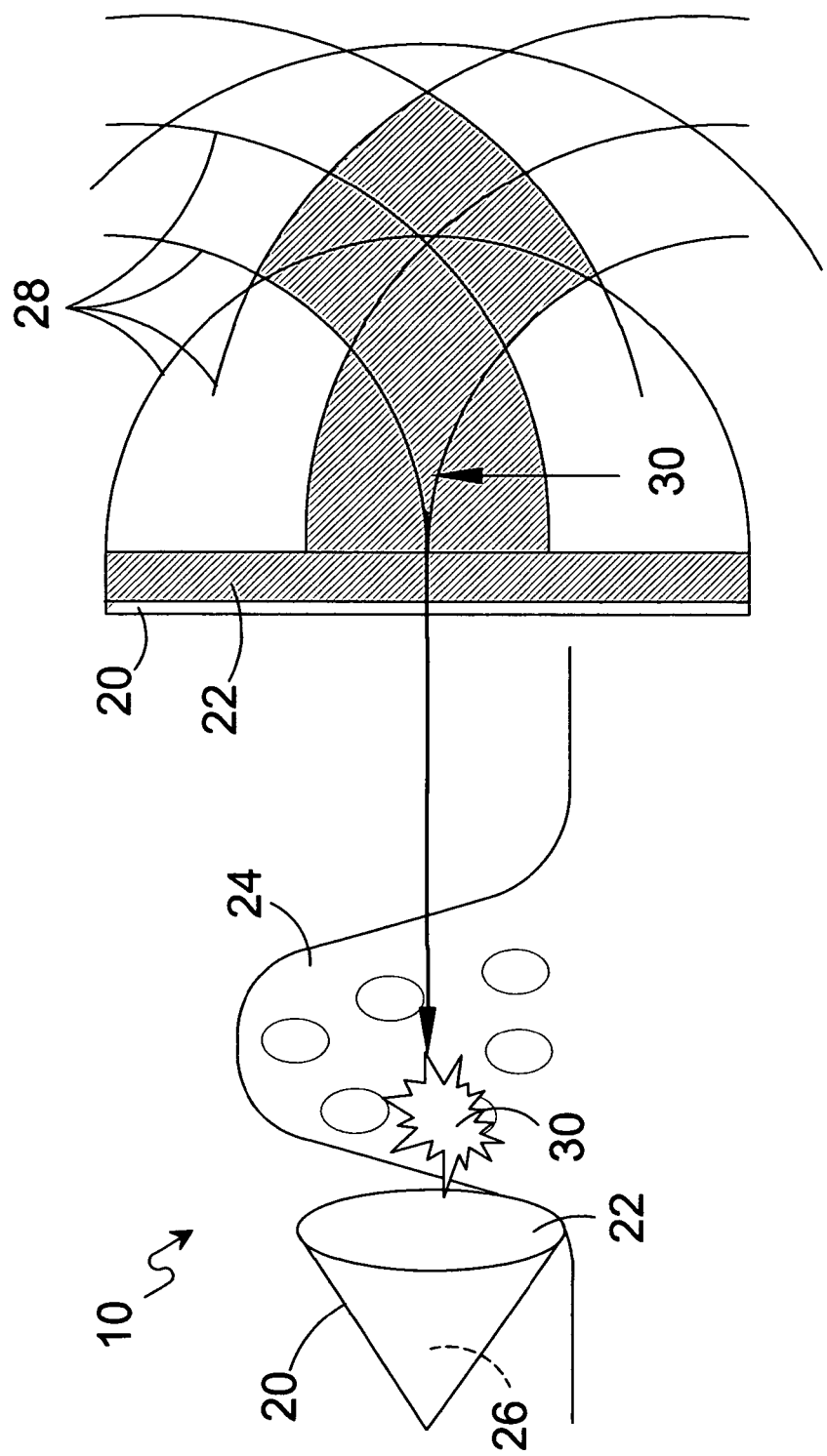
FIG. 5 is an illustrative view of adipose tissue destruction within the cavitational zone.

Referring to FIG. 5, shown is an illustrative view of adipose tissue destruction within the cavitational zone. The non-focused shock wave critical cavitational zone 30 starting from the handpiece's 20 membrane 22 interfere with the underlying structures of the skin subcutaneous adipose tissue 24 according to its density, elasticity and resonance properties. Shock waves 28 induce different effects on subcutaneous adipose tissue 24. Basically, the sonic wave 28 generated by shock wave generator 26 compromises the adipose tissue 24 cell membrane freeing the triglyceride content of the adipose cell. Elastic properties present in the vessels and nerves in the adipose tissue help to preserve these elements from shock wave damage.

Figure 6:
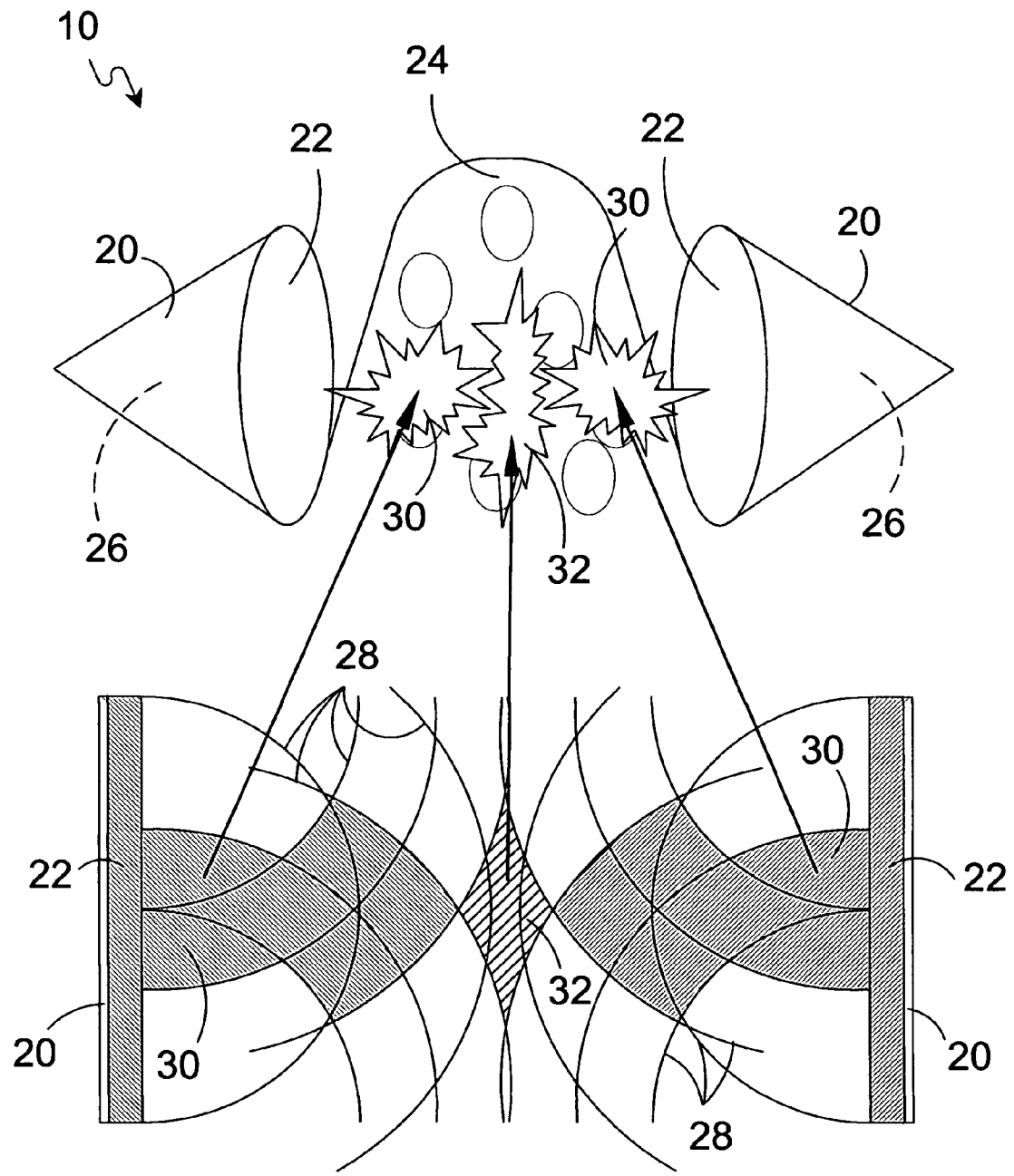
FIG. 6 is a pair of opposing applicators creating an interferential clash point.

Referring to FIG. 6, shown are a pair of opposing applicators creating an interferential clash point. As illustrated, two applicators 20 are positioned on opposing sides of a desired treatment area having adipose tissue 24 therein. As aforementioned, the applicators 20 having shock wave generator 26 generate shock waves 28 having a cavitational zone 30 extending from the handpiece applicator 20 cone-shaped which destroys adipose tissue within the cavitational zone 30. When two opposing applicators 20 are used a third interferential zone 32 is created between the opposing cavitational zones 30 which also destroys adipose tissue freeing its triglyceride content.

Figure 7:
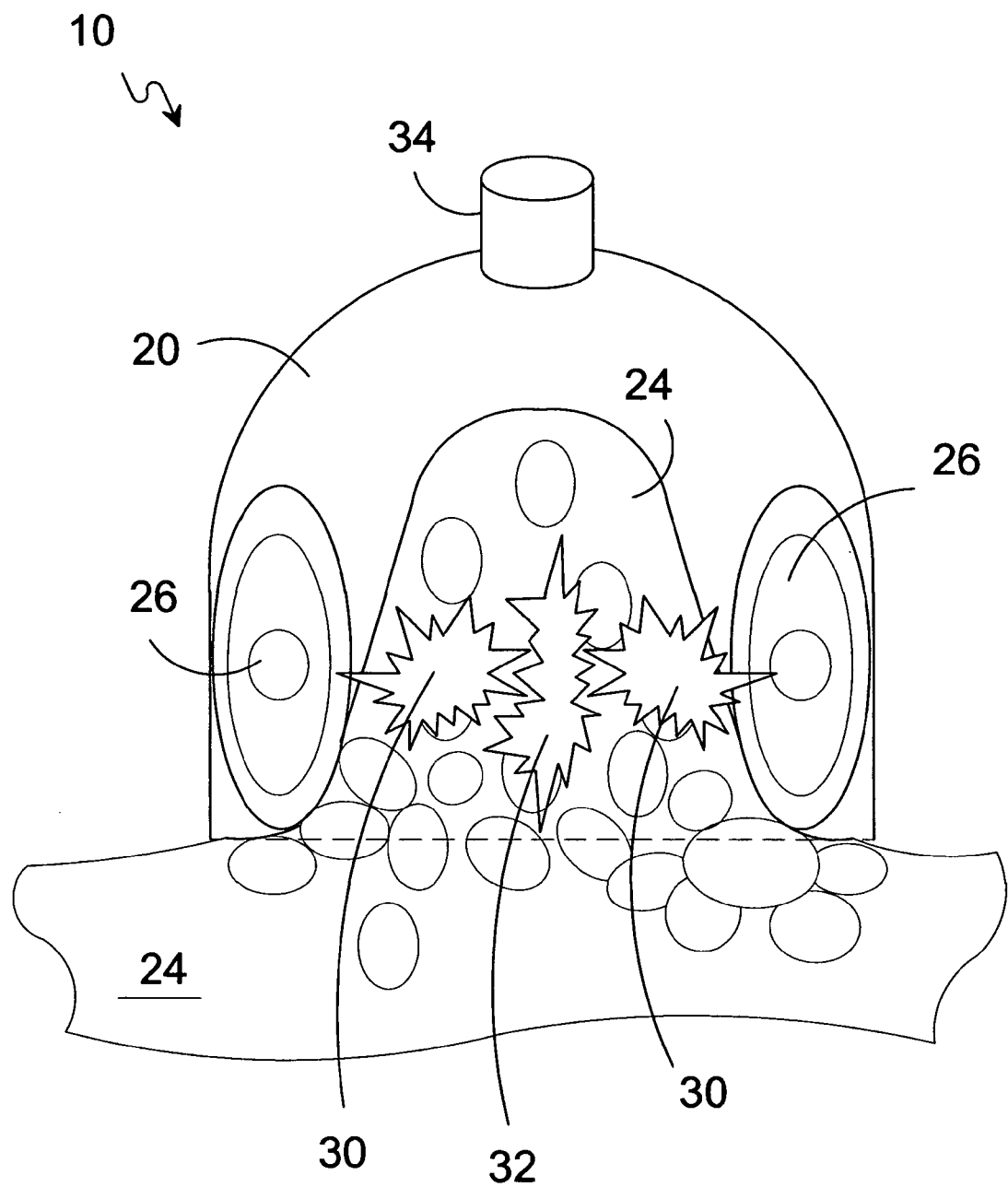
FIG. 7 is an additional handpiece applicator of the present invention.

Referring to FIG. 7, shown is an additional handpiece applicator. The present invention 10 is a device for treatment of adipose tissue comprising two or more ultrasound generators 26 positioned on opposing sides of the treatment area 24 each generating a non-focused wave forming cavitational zone 30 that converge forming a clash zone 32 with the treatment area 24 therein. Ultrasound generators 26 are contained within a housing 20 having a port 34 for connection of a source of vacuum within said housing 20 for positioning a treatment area 24 between said generators 26. The cup shaped applicator 20 may be used for thin adipose tissue layer or for rejuvenation purposes in the face skin or neck skin or anywhere on the body that may be useful for the treatment of the adipose tissue or the treatment of the skin.

Figure 8:
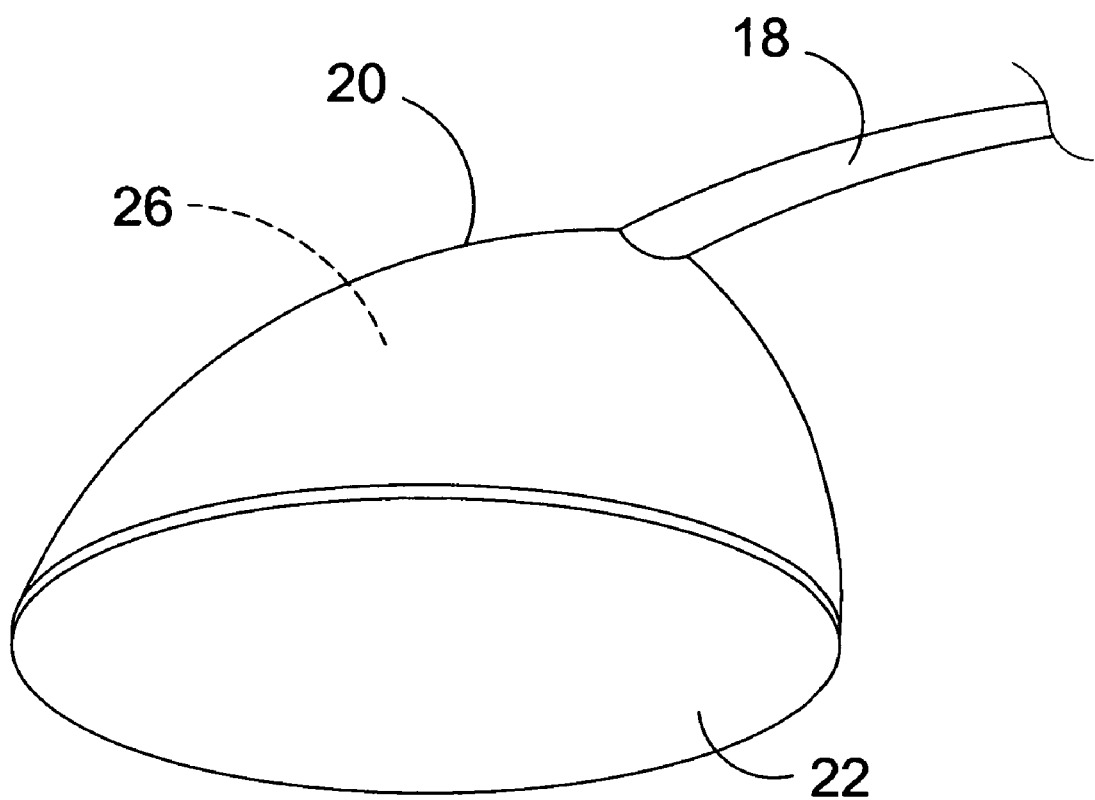
FIG. 8 is a perspective view of an applicator having an oval shape.

Referring to FIG. 8, shown is a perspective view of an applicator having an oval shape. The applicator 20 has a housing containing the coil 26 of the shock wave generator which is in electrical communication 18 with the pulse generator 14. The applicator housing 20 has an oval shaped membrane 22 with acoustic properties similar to body tissue that provides an interface between the applicator and the region to be treated. A medium such as oil, water or a water-based gel may be used for acoustic coupling between the applicator oval membrane 22 and the skin 24.

What is claimed is new and desired to be protected by Letters Patent is set forth In the appended claims:

1. A system for treatment of a skin fold with adipose tissue therein, the system comprising:
   a) an electronic pulse generator that delivers electronic pulses to first and second applicators;
   b) each applicator having a conical housing with a narrow end and an opposed wide end, a shock wave generator positioned in each said conical housing closer to the narrow end than said wide end, each shock wave generator being a substantially flat coil disposed transverse to a central longitudinal axis of its respective conical housing, each shock wave generator configured to generate a non-focused shock wave on the skin fold, each conical housing having a planar resonance membrane disposed at the wide end thereof, each non-focused shock wave going directly from its respective flat coil to its respective resonance member; and
   c) wherein when the first and second applicators are positioned directly opposite each other with one on either side of the skin fold, each non-focused shock wave creates a cavitational zone that starts out from its respective resonance membrane shaped as a cone and an interferential energy zone is formed where the shock waves clash within the skin fold, each cavitational zone and the interferential energy zone destroying the adipose tissue.

2. The system of claim 1, further comprising a sound transmitting medium placed on the resonance membrane to eliminate any air between the membrane and the skin fold during use.

3. The system of claim 2 wherein said sound transmitting medium is selected from the group consisting of water, water gel composition, and oil.

4. The system of claim 1, further comprising a processor that is configurable to deliver a sequence of pulses to the substantially flat coil within each of the applicators.

5. The system of claim 4, wherein said processor is configurable to determine at least one parameter of the non focused shock waves.

6. The system of claim 5, wherein the processor provides means to vary a pulse energy delivered to each shock wave generator and therein vary the interferential energy zone for optimal lipolytic results.

7. The system of claim 1, wherein each of the shock wave generators has an oval shape.

8. A method of treating a skin fold having adipose tissue therein, the method comprising:
   providing a system for treatment of the skin fold, the system comprising:
      a) an electronic pulse generator that delivers electronic pulses to first and second applicators;
      b) each applicator having a conical housing with a narrow end and an opposed wide end, a shock wave generator positioned in each said conical housing closer to the narrow end than said wide end, each shock wave generator being a substantially flat coil disposed transverse to a central longitudinal axis of its respective conical housing, each shock wave generator configured to generate a non-focused shock wave on the skin fold, each conical housing having a resonance membrane disposed at the wide end thereof;
   positioning the first and second applicators in an opposed manner 180 degrees apart with one on either side of the skin fold;
   generating a non-focused shock wave from each substantially flat coil, each non-focused shock wave going directly from its respective flat coil to its respective resonance member, each non-focused shock wave moves transversely through the skin fold; and
   forming an interferential energy zone where the shock waves clash within the skin fold, such that each cavitational zone and the interferential energy zone destroy the adipose tissue within the skin fold.

* * * * *